(12) United States Patent
Shih (10) Patent No.: US 11,293,576 B2
(45) Date of Patent: Apr. 5, 2022

(54) GAS SUPPLY CONNECTOR

(71) Applicant: Caremed Supply Inc., New Taipei (TW)

(72) Inventor: Pao-Ming Shih, New Taipei (TW)

(73) Assignee: Caremed Supply Inc., New Taipei (TW)

( * ) Notice: Subject to any disclaimer, the term of this patent is extended or adjusted under 35 U.S.C. 154(b) by 86 days.

(21) Appl. No.: 17/006,957

(22) Filed: Aug. 31, 2020

(65) Prior Publication Data

US 2022/0065379 A1 Mar. 3, 2022

(51) Int. Cl.

| | |
|---|---|
| *A61H 9/00* | (2006.01) |
| *A61M 39/10* | (2006.01) |
| *F16L 37/08* | (2006.01) |
| *F16L 37/56* | (2006.01) |
| *F16L 39/02* | (2006.01) |
| *F16L 37/098* | (2006.01) |
| *F16L 37/084* | (2006.01) |

(52) U.S. Cl.
CPC ............ *F16L 39/02* (2013.01); *A61H 9/0078* (2013.01); *F16L 37/56* (2013.01); *A61H 2201/1409* (2013.01); *A61M 39/105* (2013.01); *F16L 37/0847* (2013.01); *F16L 37/0982* (2013.01); *F16L 37/0985* (2013.01); *F16L 2201/60* (2013.01)

(58) Field of Classification Search
CPC . F16L 39/02; F16L 39/00; F16L 37/56; F16L 11/22; F16L 2201/60; F16L 37/0982; F16L 37/0985; F16L 41/001; F16L 37/098; F16L 37/0847; A61H 9/0078; A61H 2201/1409; A61M 39/105; A61M 39/1011
USPC ...... 285/124.5, 120.1, 124.1, 124.4, 921, 82
See application file for complete search history.

(56) References Cited

U.S. PATENT DOCUMENTS

| | | | | |
|---|---|---|---|---|
| 4,793,639 | A * | 12/1988 | Glover | ......................... 285/921 |
| 4,804,208 | A * | 2/1989 | Dye | ........................ F16L 37/56 |
| | | | | 285/124.4 |
| 4,900,065 | A * | 2/1990 | Houck | .................. F16L 37/098 |
| | | | | 285/124.4 |
| 4,969,879 | A * | 11/1990 | Lichte | ................. F16L 37/0985 |
| 5,219,185 | A * | 6/1993 | Oddenino | ............... F16L 37/56 |
| | | | | 285/921 |
| 5,688,254 | A * | 11/1997 | Lopez | ................ A61M 39/1011 |
| 5,884,943 | A * | 3/1999 | Katzer | ................ F16L 37/0985 |
| 6,213,978 | B1 * | 4/2001 | Voyten | |

(Continued)

*Primary Examiner* — Matthew Troutman
*Assistant Examiner* — William S. Choi (57) ABSTRACT

A gas supply connector of the present invention includes a gas supply member and two fasteners, wherein the gas supply member has a main body and multiple tubes; the fastener includes a buckling portion, a pressing portion and a neck portion. The pressing portion has an inner layer body and an outer layer body. The neck portion contracts from two lateral ends toward the center to form a tapered section, and the outer surface of the neck portion is arranged with multiple reinforcing ribs. The present invention through the neck portion reduces the force required for pressing the fastener to deform by the user, and through the reinforcing ribs increases the structural strength of the neck portion to prevent the fastener from breaking; in addition, the inner layer is made of plastic, and outer layer body is made of soft material, so as to improve the comfort of pressing fastener.

9 Claims, 7 Drawing Sheets

(56) References Cited

U.S. PATENT DOCUMENTS

| | | | | |
|---|---|---|---|---|
| 6,609,732 | B1* | 8/2003 | Souvatzidis | F16L 37/56 |
| | | | | 285/124.5 |
| 7,490,620 | B2* | 2/2009 | Tesluk | A61M 39/105 |
| | | | | 285/124.5 |
| 8,136,844 | B1* | 3/2012 | Liu | F16L 37/56 |
| | | | | 285/124.3 |
| 8,801,046 | B2* | 8/2014 | Shinoda | F16L 37/56 |
| | | | | 285/124.4 |
| 9,316,358 | B2* | 4/2016 | Shih | A61H 9/0078 |
| 9,534,721 | B2* | 1/2017 | Lombardi, III | F16L 37/56 |
| 10,998,665 | B2* | 5/2021 | McKevitt | A61M 39/105 |
| 2004/0232696 | A1* | 11/2004 | Andre | F16L 37/0985 |
| | | | | 285/921 |
| 2009/0188575 | A1* | 7/2009 | Williams | A61M 39/1011 |
| 2009/0192463 | A1* | 7/2009 | Nardeo | |
| 2009/0287140 | A1* | 11/2009 | Rittman, III | |
| 2015/0061282 | A1* | 3/2015 | Faldt | A61M 39/105 |
| | | | | 285/124.5 |
| 2019/0162345 | A1* | 5/2019 | Lee | F16L 37/56 |

\* cited by examiner

GAS SUPPLY CONNECTOR

FIELD OF THE INVENTION

The present invention relates to a gas supply connector applied to inflation massage device, and more particularly, to a gas supply connector with fasteners on its both sides to avoid separation because of pulling.

BACKGROUND

In order to solve the situation that patients have stayed in bed for a long time, and their limbs are often unable to move flexibly, resulting in poor functioning of the body and in turn causing more complications, companies in this industry have developed a compression sheath of a gas supply device connected to a gasbag. Using the change of the gasbag volume to apply pressure onto the local area of the body, it can assist the body to speed up the return of normal operation.

However, because of gas moving repeatedly in and out, momentary force from outputting gas by supply device will cause the connection between the gas supply device and the gasbag to easily fall off. Therefore, an additional fastening structure has been designed into the connection assembly between the gas supply device and the gasbag to prevent the male and female connectors themselves from being separated. However, the conventional gas supply connection are all made of plastic injection molding, and accordingly the user often feels uncomfortable when pressing the fasteners, and the fasteners are often not easily deformed by pressing, or insufficient structural strength causes breakage and damage after repeated use. In view of this, it is necessary to improve and make innovation in the gas supply connector.

SUMMARY

The main purpose of the present invention is to provide a gas supply connector to reduce the force required for pressing the fastener to deform by the user, and to design a reinforced structure to increase the structural strength of the fastener, which improves the lack that the fastener easily breaks at deformation position after using many times.

The secondary purpose of the present invention is to adopt a double-layer design in the pressing part to improve the comfort of pressing fastener.

Another purpose of the present invention is to design the surface of the connector with a foolproof structure to prevent incorrect insertion and a display pattern that indicates the inflation massage portion, so as to improve practicability and convenience of the gas supply connector.

In order to achieve the above-mentioned purpose, the gas supply connector of the present invention includes a gas supply member and a plurality of fasteners. The gas supply member comprises a main body and a plurality of tubes. The inside of the main body forms a plurality of gas passages along a front-rear insertion direction, and the opposite ends of the gas passage are respectively connected to different tubes; the fasteners are respectively connected to the left-right opposite sides of the main body, and the fastener includes a buckling portion, a pressing portion, and a neck portion between the buckling portion and the pressing portion. The pressing portion has an inner layer body integrally formed with the neck portion and an outer layer body enveloping the inner layer body. The neck portion contracts from two lateral ends toward the center to form a tapered section, and the outer surface of the neck portion is provided with a plurality of reinforcing ribs.

In one preferred embodiment, a plurality of anti-slip strips are formed on a surface of the pressing portion, and a slope projection is formed at an end of the pressing portion; the neck portion and the buckling portion have a first thickness, the main body has a second thickness larger than the first thickness, and the pressing portion has a third thickness larger than the second thickness.

Wherein, the outer surface of the inner layer body has a plurality of protrusions, and a plurality of depressions corresponding to the protrusions are formed on the inner surface of the outer layer body; the inner layer body and the outer layer body are composed of different materials, a first material and a second material, respectively.

In addition, a display pattern is arranged on a surface of the main body; the front of the neck portion is a form of contracted arc, and the rear of the neck portion is a slope-tapered form. The reinforcing ribs are respectively arranged on the upper and lower surfaces of the neck portion. A first rib and a second rib are respectively formed at the front and rear ends of the neck portion, and the height of the second rib is larger than that of the first rib.

The outer periphery of the main body is arranged with a ring protrusion, and the ring protrusion is constructed with a recess extending along the front-rear insertion direction. The outer layer body is a bag made of a deformable material, the bag has an opening with a diameter smaller than the third thickness, and the diameter of the opening is larger than the first thickness of the neck portion.

The feature of the present invention features a tapered section and a plurality of reinforcing ribs designed into the neck portion of the fastener, accordingly to reduce the force required for pressing the fastener to deform by a user, and the structural strength of the neck portion increases by reinforcing ribs. In addition, in the pressing portion the inner layer body is made of plastic, and the outer layer body is made of soft material, so as to improve the comfort of pressing fastener. And there are multiple mutual corresponding fastening-against mechanisms formed between the inner and outer layer bodies to prevent the inner and outer layer bodies from being separated from each other.

DETAILED DESCRIPTION OF PREFERRED EMBODIMENTS

Figure 1:
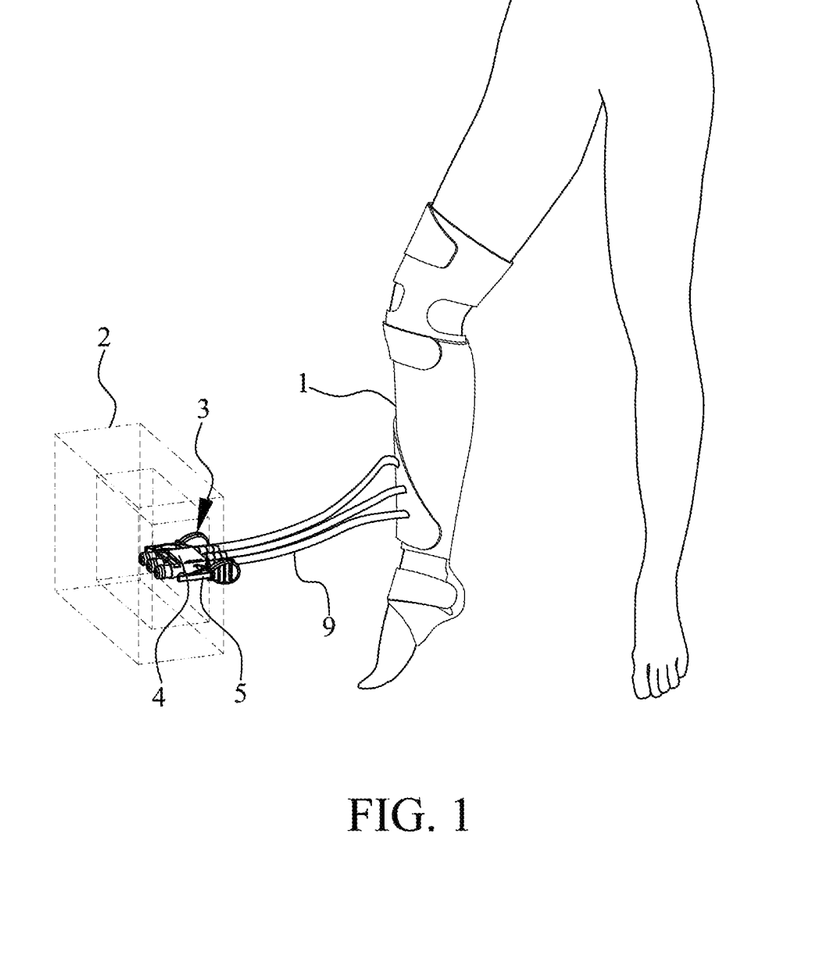
FIG. 1 is a schematic illustrating a gas supply connector of the present invention connected with the gas supply device to be applied to the thigh.

In order to further understand the structure, usage and features of the present invention more clearly and in detail, the present invention is described in detail below with references to the accompanying drawings and specific preferred embodiments:

Please refer to FIG. 1. The present invention relates to a gas supply connector 3 applied to an inflatable massage element 1. The gas supply connector 3 is used to assembled to a gas supply device 2 so that the gas supply device 2 supplies gas through the gas supply connector 3 intermittently to the inflatable massage element 1, which makes the inflatable massage element 1 capable of alternately expanding and contracting to achieve the effect of massaging the thigh.

Figure 2:
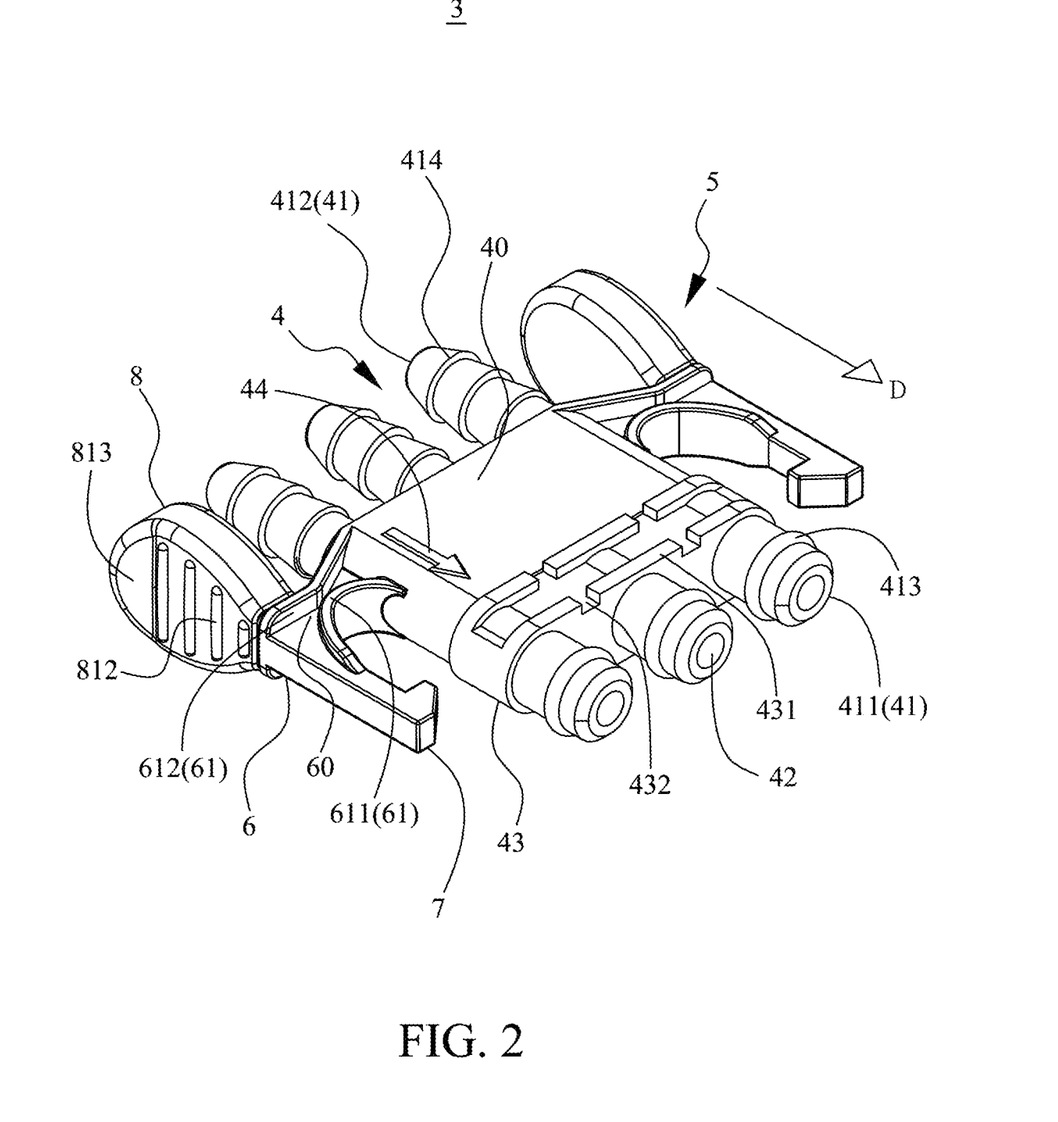
FIG. 2 is a schematic illustrating perspective view of the gas supply connector according to the present invention.
Figure 3:
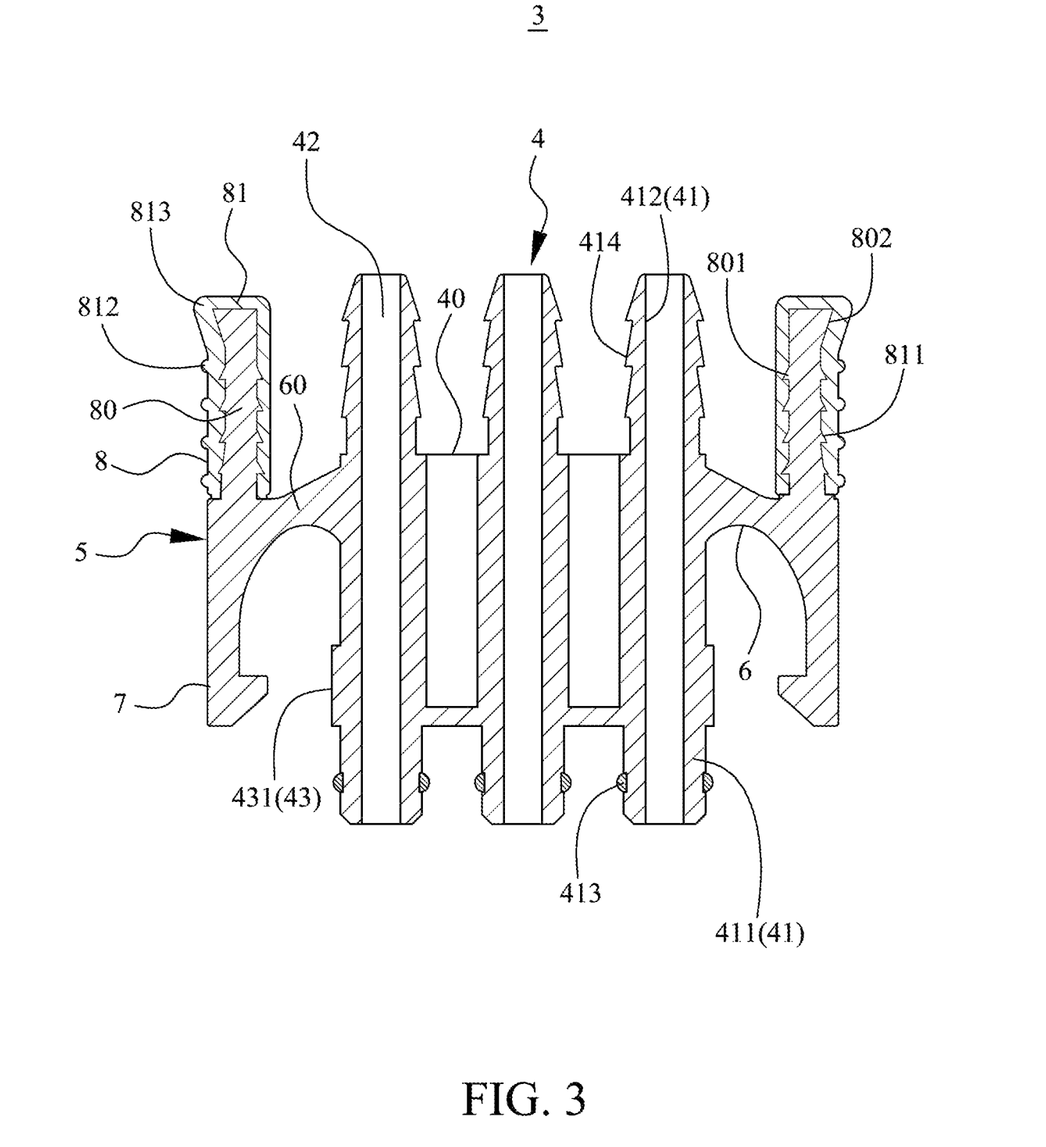
FIG. 3 is a schematic illustrating cross-sectional view of the gas supply connector of FIG. 2.
Figure 4:
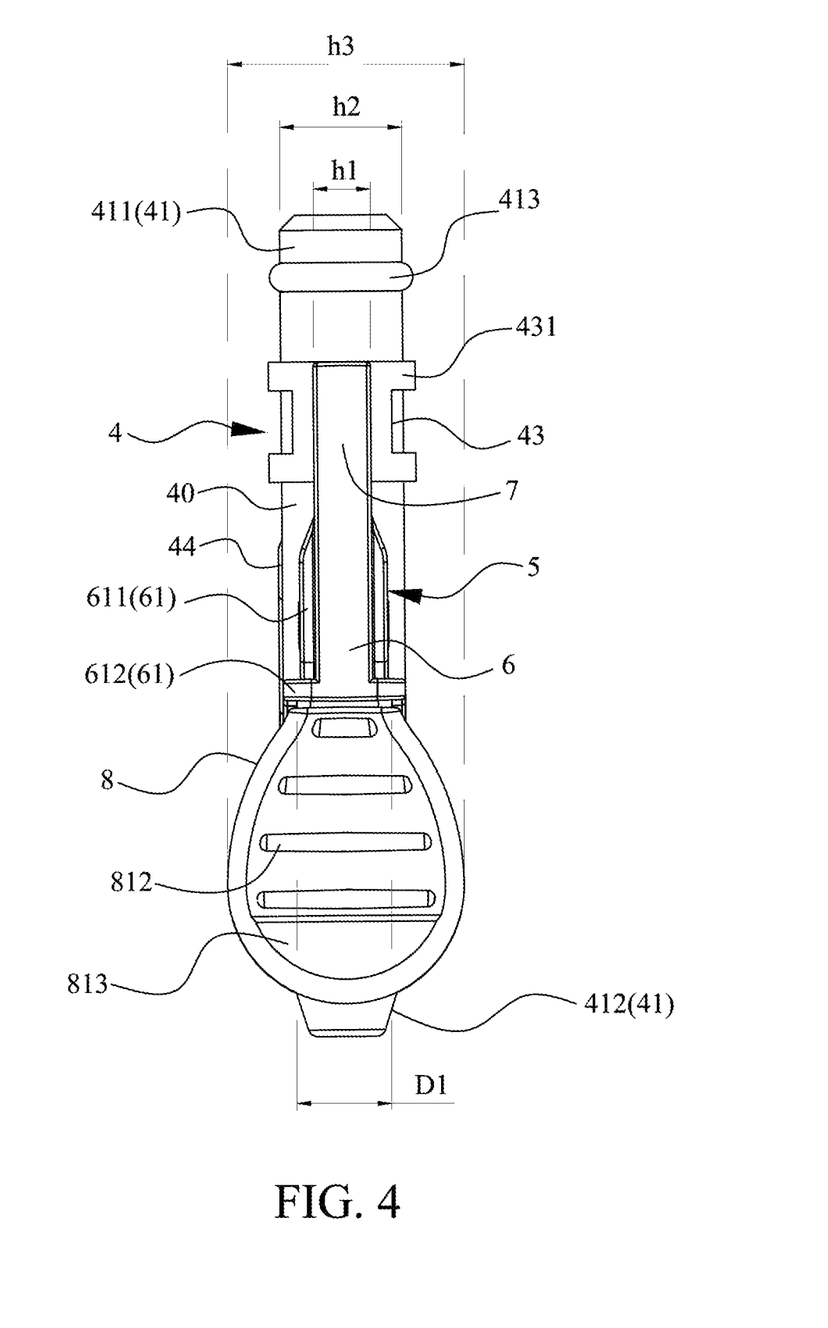
FIG. 4 is a schematic illustrating side view of the gas supply connector of the present invention.
Figure 5:
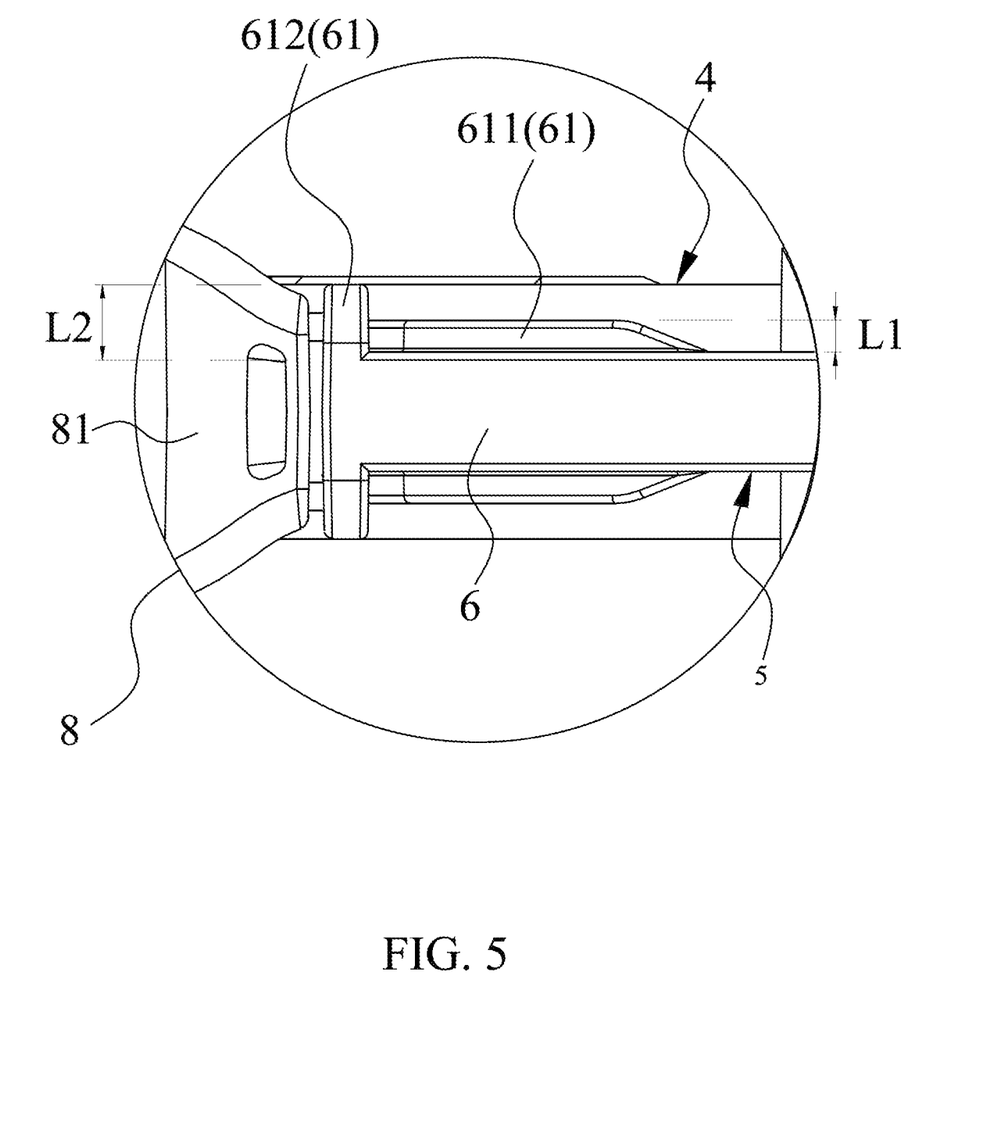
FIG. 5 is a schematic illustrating enlarged view of FIG. 4.

Please refer to FIGS. 1 to 3. The gas supply device 2 of the present invention includes a gas supply member 4 and two fasteners 5. The gas supply member 4 has a main body 40 and a plurality of tubes 41 arranged on opposite sides of the main body 40. Inside the main body 40 along a front-rear insertion direction D constitute a plurality of gas passages 42. Each gas passage 42 communicates with a first tube 411 at an insertion end, and the gas passage 42 communicates with a second tube body 412 at a departing end. The first tube 411 shows a smooth surface and has a ring groove (not shown in the figure) to be installed with a gasket 413. The surface of the second tube 412 has a plurality of inverted cone blocks 414, wherein the second tube 412 is used for being assembled to a gas tube 9 and can prevent the gas tube 9 from easily being separated from the gas supply member 4. The first tube 411 is used for being inserted into a socket of the gas supply device 2 (not shown in the figure).

The surface of the main body 40 is constructed with a foolproof structure 43 to prevent the user from inserting in the wrong direction and a display pattern 44 for indicating the inflation massage region. The foolproof structure 43 is adjacent to the first tube 411, and includes a ring protrusion 431 perpendicular to the front-rear insertion direction D and a recess 432 parallel to the front-rear insertion direction D. The ring protrusion 431 surrounds the outer periphery of the main body 40, and the recess 432 passes through the ring protrusion 431; the display pattern 44 is aligned with one of the first tube 411 and the second tube 412. In the present embodiment, the fool proof structure 43 may be arranged with multiple recesses 432, and the recesses 432 are all arranged on the same surface of the main body 40; in addition, the display pattern 44 is set as an arrow shape. However, this is only for the convenience of illustration. The display pattern 44 can also be designed as a form of triangle, round mark, text, or symbol.

Please refer to FIGS. 2 to 5 again. The fasteners 5 are respectively connected to the left and right sides of the main body 40. The fastener 5 includes a neck portion 6, a buckling portion 7 and a pressing portion 8. The neck portion 6 is connected to a rear position of the main body 40, and the buckling portion 7 and the pressing portion 8 are formed and respectively extended from opposite positions (front and rear) of the neck portion 6. Wherein, the pressing portion 8 has an inner layer body 80 integrally formed with the neck portion 6 and an outer layer body 81 enveloping the inner layer body 80 (see FIG. 3). The pressing portion 8 also shows an elliptical shape to increase the area for being touched by the user's hand and facilitate the pressing of the fastener 5; the outer surface of the inner layer body 80 has a plurality of protrusions 801, and the inner surface of the outer layer body 81 is formed with a plurality of depressions 811 corresponding to the protrusions 801. In addition, the inner layer body 80 and the outer layer body 81 are composed of different materials, a first material and a second material, respectively. The first material may be a plastic material, and the second material may be a silicone material which is soft and deformable.

In one preferred embodiment, a plurality of anti-slip strips 812 arranged in parallel are formed on the surface of the outer layer body 81 of the pressing portion 8, and slope projections 802, 813 formed at the end of both the inner layer body 80 and the outer layer body 81 of the pressing portion 8. Please refer to FIG. 4, the neck portion 6 and the buckling portion 7 have a first thickness h1, the main body 40 has a second thickness h2 greater than the first thickness h1, and the pressing portion 8 has a third thickness h3 greater than the second thickness h2. In addition, the outer layer body 81 is configured as the form of a bag, the bag has an opening with a diameter D1 smaller than the third thickness h3, and the opening diameter D1 is greater than the first thickness h1 of the neck portion 6.

In addition, please refer to FIGS. 2 and 5 again, the neck portion 6 contracts from two lateral ends toward the center to form a tapered section 60, and the outer surface of the neck portion 6 is provided with a plurality of reinforcing ribs 61. The front of the neck portion 6 is a form of contracted arc, and the rear of the neck portion 6 is a slope-tapered form. The reinforcing ribs 61 are respectively disposed on the upper and lower surfaces of the neck portion 6. Furthermore, a first rib 611 showing a curved shape and a second rib 612 showing a v-shaped are respectively formed on the front and rear ends of the neck portion 6. Wherein, the first rib 611 has a first height L1, the second rib 612 has a second height L2, and the first height L1 is lower than the second height L2. Moreover, the first rib 611 and the second rib 612 are not in contact. The inflection point of the first rib 611 and the turning point of the second rib 612 are arranged in an offset manner in the front-rear direction.

Figure 6A:
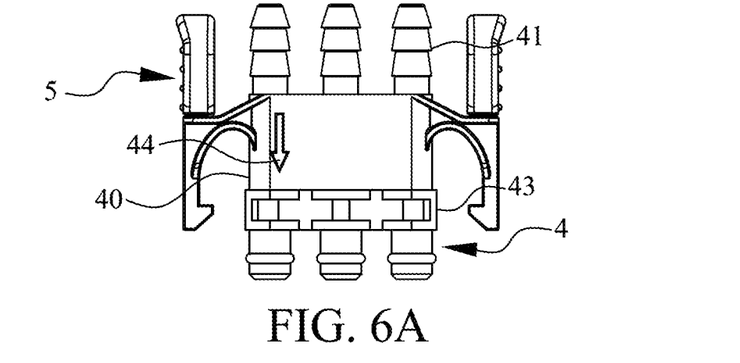
FIGS. 6A to 6C are schematic illustrating the display pattern located at different positions.
Figure 6B:
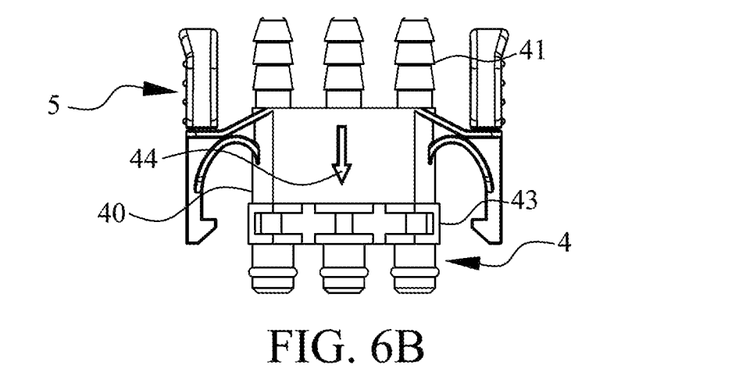
Figure 6C:
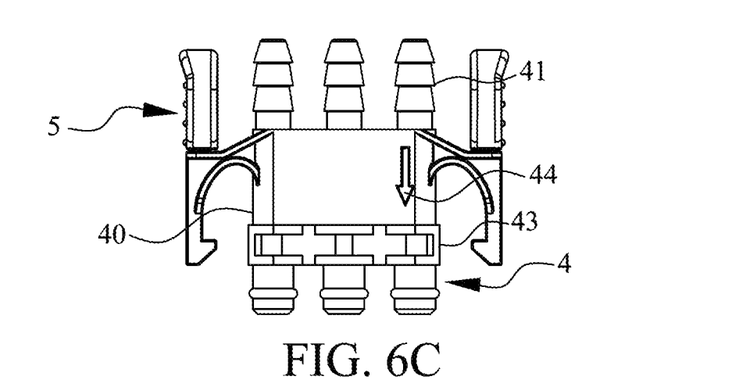
Figure 7:
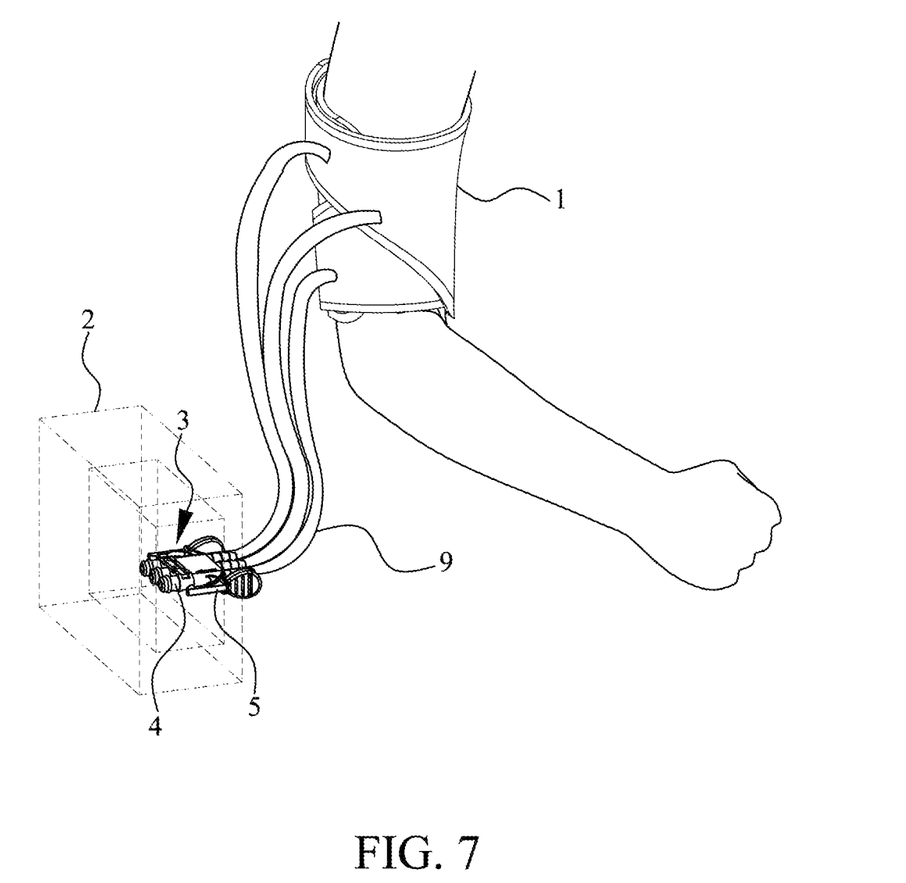
FIG. 7 is a schematic illustrating the gas supply connector of the present invention applied to the arm according to the display pattern.

Please refer to FIG. 6A, as can be seen from the position of the display pattern 44 on the left, the inflatable massage element 1 connected to the gas supply connector 3 is applied to the positions of thigh and calf; please refer to FIG. 6B, when the display pattern 44 is located in the center position, the inflatable massage element 1 connected to the gas supply connector 3 can be applied to the ankle position (not shown in the figure); please refer to FIG. 6C, when the display pattern 44 is on the right side, the inflatable massage element 1 connected to the gas supply connector 3 is applied to the arm position (see FIG. 7). However, the position of the display pattern 44 mentioned above corresponding to the massage region is only for the convenience of illustration, that is, shape and position of the display pattern 44 corresponding to the massage region can be set according to actual usage conditions.

What is claimed is:
1. A gas supply connector, comprising:
a gas supply member comprising a main body and a plurality of tubes, wherein the inside of the main body forms a plurality of gas passages along a front-rear insertion direction, and the opposite ends of the gas passage are respectively connected to different tubes; and
a plurality of fasteners, respectively connected to the left-right opposite sides of the main body, and including a buckling portion, a pressing portion, and a neck portion between the buckling portion and the pressing portion, wherein the pressing portion has an inner layer body integrally formed with the neck portion and an outer layer body enveloping the inner layer body, and the neck portion contracts from two lateral ends toward the center to form a tapered section, and the outer surface of the neck portion is arranged with a plurality of reinforcing ribs.

2. The gas supply connector according to claim 1, wherein a plurality of anti-slip strips are formed on a surface of the pressing portion, and a slope projection is formed at an end of the pressing portion.

3. The gas supply connector according to claim 1, wherein the neck portion and the buckling portion have a first thickness, the main body has a second thickness larger than the first thickness, and the pressing portion has a third thickness larger than the second thickness.

4. The gas supply connector according to claim 3, wherein the outer layer body is a bag made of a deformable material, the bag has an opening with a diameter smaller than the third thickness, and the diameter of the opening is larger than the first thickness of the neck portion.

5. The gas supply connector according to claim 1, wherein the outer surface of the inner layer body has a plurality of protrusions, and a plurality of depressions corresponding to the protrusions are formed on the inner surface of the outer layer body, and wherein the inner layer body and the outer layer body are composed of different materials, a first material and a second material, respectively.

6. The gas supply connector according to claim 1, wherein a display pattern is arranged on a surface of the main body.

7. The gas supply connector according to claim 1, wherein the front of the neck portion is a form of contracted arc and the rear of the neck portion is a slope-tapered form.

8. The gas supply connector according to claim 1, wherein the reinforcing ribs are respectively arranged on the upper and lower surfaces of the neck portion, and wherein a first rib and a second rib are respectively formed at the front and rear ends of the neck portion, and the height of the second rib is larger than that of the first rib.

9. The gas supply connector according to claim 1, wherein the outer periphery of the main body is arranged with a ring protrusion, and the ring protrusion is constructed with a recess extending along the front-rear insertion direction.

* * * * *